(12) United States Patent
Khare et al.

(10) Patent No.: US 12,180,465 B2
(45) Date of Patent: Dec. 31, 2024

(54) TRANSGLUTAMINASE NANOFLOWERS

(71) Applicant: INDIAN INSTITUTE OF TECHNOLOGY DELHI, New Delhi (IN)

(72) Inventors: Sunil Kumar Khare, New Delhi (IN); Syeda Warisul Fatima, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 663 days.

(21) Appl. No.: 17/406,928

(22) Filed: Aug. 19, 2021

(65) Prior Publication Data

US 2022/0056432 A1 Feb. 24, 2022

(30) Foreign Application Priority Data

Aug. 20, 2020 (IN) .............................. 202011035812

(51) Int. Cl.
C12N 11/14 (2006.01)
(52) U.S. Cl.
CPC ................................... *C12N 11/14* (2013.01)
(58) Field of Classification Search
CPC ...... C12N 11/18; C12N 9/1044; C12N 11/14; C12Y 203/02013
See application file for complete search history.

(56) References Cited

PUBLICATIONS

Ajorlou, E. and Khosroushahi, A.Y., 2017. Trends on polymer-and lipid-based nanostructures for parenteral drug delivery to tumors. Cancer chemotherapy and pharmacology, 79(2), pp. 251-265.
Avinash P. Ingle, Mahendra Rai, "Copper nanoflowers as effective antifungal agents for plant pathogenic fungi", Journals The Institution of Engineering and Technology, 2017 vol. 11 Iss.5, pp. 546-551, https://www.ncbi.nlm.nih.gov/pubmed/28745287.
Chan, S.K. and Lim, T.S., 2019. Bioengineering of microbial transglutaminase for biomedical applications. Applied microbiology and biotechnology, 103(7), pp. 2973-2984.
Duarte, L., Matte, C.R., Bizarro, C.V. and Ayub, M.A.Z., 2020. Review transglutaminases: part II—industrial applications in food, biotechnology, textiles and leather products. World Journal of Microbiology and Biotechnology, 36(1), pp. 1-20.
Fatima, S.W. and Khare, S.K., 2018. Current insight and futuristic vistas of microbial transglutaminase in nutraceutical industry. Microbiological research, 215, pp. 7-14.
Fatima, S.W., Tiwari, R. and Khare, S.K., 2019. Utilization of agro-industrial waste for production of Transglutaminase from Streptomyces mobaraensis. Bioresource technology, 287, p. 121391.

Folk, J.E. and Cole, P.W., 1965. Structural requirements of specific substrates for guinea pig liver transglutaminase. Journal of Biological Chemistry, 240(7), pp. 2951-2960.
Gajšek, M., Jancic, U., Vasic, K., Knez, Ž. and Leitgeb, M., 2019. Enhanced activity of immobilized transglutaminase for cleaner production technologies. Journal of Cleaner Production, 240, p. 118218.
Ge J., Lei. J., and Zare R. 2012. Protein-inorganic hybrid nanoflowers. Nature Nanotechnology, 7, pp. 428-432.
Irimie, A.I., Sonea, L., Jurj, A., Mehterov, N., Zimta, A.A., Budisan, L., Braicu, C. and Berindan-Neagoe, I., 2017. Future trends and emerging issues for nanodelivery systems in oral and oropharyngeal cancer. International journal of nanomedicine, 12, p. 4593.
Lamberti, M., Zappavigna, S., Sannolo, N., Porto, S. and Caraglia, M., 2014. Advantages and risks of nanotechnologies in cancer patients and occupationally exposed workers. Expert opinion on drug delivery, 11(7), pp. 1087-1101.
Lee, S.W., Cheon, S.A., Kim, M.I. and Park, T.J., 2015. Organic-inkanic hybrid nanoflowers: types, characteristics, and future prospects. Journal of nanobiotechnology, 13(1), pp. 1-10.
Miwa, N., 2020. Innovation in the food industry using microbial transglutaminase: Keys to success and future prospects. Analytical Biochemistry, p. 113638.
Rana, V. and Sharma, R., 2019. Recent advances in development of nano drug delivery. In Applications of Targeted Nano Drugs and Delivery Systems (pp. 93-131). Elsevier.
Seung Woo Lee et al., "Organic-inorganic hybrid nanoflowers: types, characteristics, and future prospects", Journal of Nanobiotechnology (2015) 13:54, https://www.ncbi.nlm.nih.gov/pmc/articles/PMC4559159/.
Shagun Gupta et al., "Ultrasensitive transglutaminase based nanosensor for early detection of celiac disease in human", International Journal of Biological Macromolecules, (2017) 905-911; https://www.researchgate.net/publication/318605355_Ultrasensitive_transglutaminase_based_nanosensor_for_early_detection_of_celiac_disease_in_human.
Wu, P., Luo, F., Lu, Z., Zhan, Z. and Zhang, G., 2020. Improving the Catalytic Performance of Pectate Lyase Through Pectate Lyase/Cu3 (PO4) 2 Hybrid Nanoflowers as an Immobilized Enzyme. Frontiers in Bioengineering and Biotechnology, 8, p. 280.
Wu, X., Hou, M. and Ge, J., 2015. Metal-organic frameworks and inorganic nanoflowers: a type of emerging inorganic crystal nanocarrier for enzyme immobilization. Catalysis Science & Technology, 5(12), pp. 5077-5085.
Yan-Kui Luo et al., "Pure copper phosphate nanostructures with controlled growth: a versatile support for enzyme immobilization", Royal Society of Chemistry, 2017, 19.2996-3002, https://pubs.rsc.org/en/content/articlelanding/2017/ce/c7ce00466d#!divAbstract.

*Primary Examiner* — Thane Underdahl
(74) *Attorney, Agent, or Firm* — Foley & Lardner LLP (57) ABSTRACT

The present invention relates to novel immobilized nanoflowers made of Transglutaminase (TGase), a method for their synthesis and applications thereof. The Transglutaminase nanoflowers of the present invention are catalytically more active without mass transfer limitation, stable and reusable, wherein the overall flower is in the nano-range, is homo-dispersed and small-sized, and wherein Transglutaminase functions both as a cross-linking enzyme and as a seeding template.

15 Claims, 10 Drawing Sheets
(9 of 10 Drawing Sheet(s) Filed in Color)

Flaky formation- petals design to bud synthesis of TGase nanoflowers

Buds transforming into flower- opening up TGase nanoflowers

Open blooming nanoflowers pockets for cargos

TRANSGLUTAMINASE NANOFLOWERS

FIELD OF INVENTION

The present invention relates to the broad field of nanotechnology. Particularly, the present invention relates to the field of biomedical nanomaterials. More particularly, the present invention relates to the enzymatic nanoflowers made of Transglutaminase (TGase) and a method of designing of Transglutaminase as an organic component mediated nanoflowers. Even more particularly, the present invention relates to a method for synthesizing Transglutaminase nanoflowers and their applications.

BACKGROUND OF THE INVENTION

Transglutaminase (TGase; EC 2.3.2.13) is an important versatile enzyme, catalyzing protein cross-linking reactions. TGase belongs to family protein-Glutamine:Amine γ-Glutamyl transferase which catalyzes acyl-transfer reactions between γ-carboxyamide groups of glutamine residues and the ε-amino group of lysine in proteins.

Figure 1:
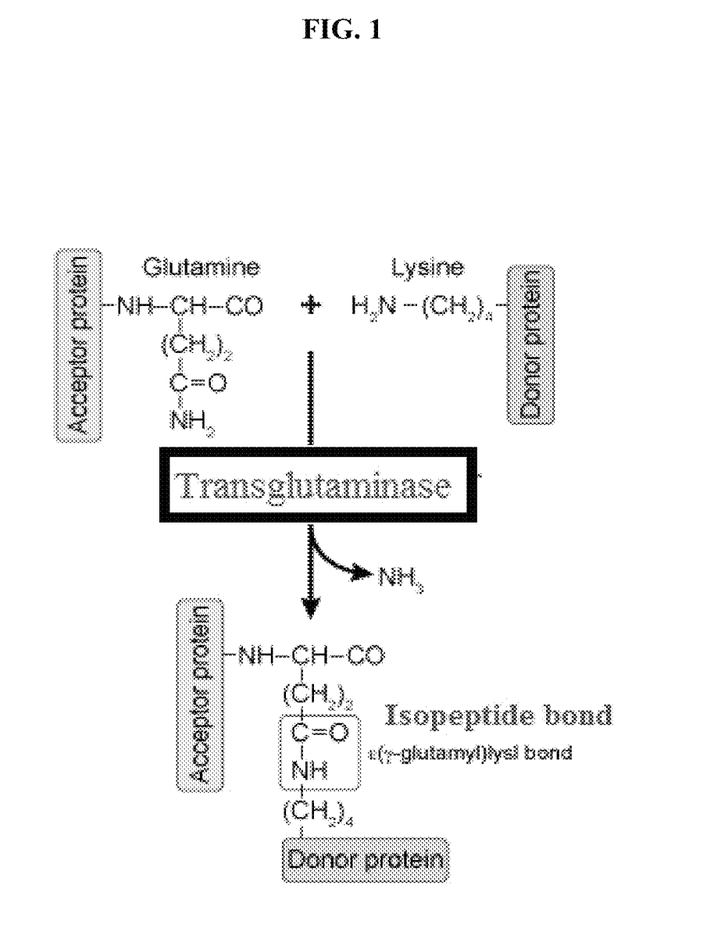
FIG. 1 illustrates the reaction catalyzed by TGase.

TGase is responsible for acyl transfer, deamidation and cross-linking protein intra- or inter chain glutamine (acyl donor) and lysine (acyl acceptor) peptide moieties. It catalyzes the reaction as shown in FIG. 1.

TGase is an important cellular cross-linking enzyme which influences the properties of cellular proteins by catalyzing iso-peptide bond. These protein networks formation mediated with TGase help in stabilizing their structural and functional integrity. The specialized role of this molecular glue enzyme i.e., the unique TGase enzyme provides formidable resistance to adverse environmental conditions. Consequent to this feature, the versatile TGases have tremendous potential use in vast areas, ranging from food and nutraceuticals, textile & leather industries to tissue engineering and other biomedical sectors.

The iso-peptide bonds (glutamyl-lysl bond) created by TGase exhibit resistance toward adverse environmental conditions. These protective structures, synthesized by microorganisms using TGase, therefore, contribute to better survival of microorganisms in hostile environments. TGase activity is pivotal to the maintenance of the normal commensal microbiota.

Further to it, the enzyme catalyzes the addition of free amines into proteins by joining the glutamine residue. Furthermore, in the absence of free amine, water becomes the acyl acceptor and the γ-carboxamide groups are deamidated to glutamic acid residues.

Transglutaminases are involved in regulating the physiological and cellular functions and have a potential role in bacterial survival. They modulate the physico-chemical properties of cellular proteins by cross-links and polymerizing them.

Further, the structural and functional attributes of the proteins are impacted by it for creating barriers and stable structures which help an organism to thrive under hostile environmental conditions e.g., spore coat structure formation.

Because of their unique site-specific cross-linking activity, they have been exploited in various industries.

The major applications of TGases are as follows:
Food industries: Meat & fish processing, dairy, surimi, noodles & pasta, bakery products etc. for enhanced structural and functional attributes like textures, restructuring (rheological), improved quality & packaging, longer shelf life, formation of edible films, reduction in allergenicity (Duarte et al., 2020; Fatima & Khare 2018; Miwa 2020).

Leather industries: Physico-mechanical properties improvement, surface functionalization of wools, textile, fibres etc to improve dyeability, softness, lustre, and tensile strength (Gajšek et al., 2019).

Biomedical applications: Diagnostic and labelling toolsite specific conjugation of antibodies/biocompatible polymers, biomaterial fabrication for tissue engineering for targeted delivery and biotherapeutics (Chan & Lim 2019).

Interestingly, Transglutaminases are costly enzymes. One enzyme unit costs US$190 (Sigma Aldrich Inc.) USA catalogue. Therefore, attempts are being made to develop active and reusable Transglutaminase to reduce their cost.

In recent years, nano-forms of proteins and enzymes have attracted a lot of interest for various bio-catalytic applications. Major among those have been nano-emulsions, nano-tubes, nano-wires, nano-crystals, dendrimers, quantum dots and nanoflowers.

A number of drug delivery vehicles such as nano-sheets, nano-fibres, nano-crystals, nano-spheres, nano-capsules, nano-diamonds, nano-cages, nano-discs and quantum dots applied in the drug targeting systems comes with certain barriers (Ajorlou & Khosroushahi, 2017, Irimie et al., 2017; Lamberti et al., 2014). The major concern lies in crossing the blood-brain barrier, cargo bio-availability and low the fraction of the cargo accumulated in the targeted area (of target release) (Rana & Sharma, 2019).

Conventionally TGases have been used in a free or immobilized form on a solid support. Transglutaminases have tremendous industrial applications. These are uniquely and extensively utilized in food processing, biomedical engineering and pharmaceuticals. These are unconventional tools for protein modification and tagging, and in preparing site-selective protein-polymer conjugates. Most of the immobilized TGase preparations suffer from mass transfer limitation and low catalytic efficiency.

Immobilized TGases are reported on supports like the thermo-responsive carboxylated poly (N-isopropylacrylamide) (pNIPAM), agarose beads (N-terminal sequence), polypropylene microporous membranes. It was applied for cross-linking the proteins bovine serum albumin (BSA), soy protein isolates etc. and PEGylation of therapeutic proteins and peptide drugs.

Various immobilized TGase along with a method of immobilization, properties and shortcoming of preparations are summarized. Conventional immobilization needs solid support upon which covalent binding of enzymes can be made. It is done at the multi-step process at a high temperature of more than 50° C. which is extensive in terms of activating the functional groups (amino) with harsh chemicals (EDC, NETS, etc.), adding spacer arms for tagging and then conjugation afterwards blocking the sites to stop the reaction. This leads to time-consuming laborious synthesis.

Table 1 below enlists some of the limitations and challenges prevailing in the current drug delivery vehicles.

TABLE 1

| Limitations and Challenges prevailing in the current drug delivery vehicles | |
|---|---|
| Nano-carrier/vehicle | Demerits |
| Nano-Liposome | Triggers immunogenic response (complement activation related pseudo allergy) Limited control of drug release-Drug leakage, expulsion and burst release Stability and industrial reproducibility issues Difficulties in sterilization Drug-loading capacity very low due to limited space |

TABLE 1-continued

Limitations and Challenges prevailing
in the current drug delivery vehicles

| Nano-carrier/vehicle | Demerits |
|---|---|
| Carbon nanotubes | Very expensive, unclear mechanism of action<br>High Toxicity<br>Non-uniformity in morphology and structure<br>Off-target release of cargo |
| Nano-micelles | Surface modifications required: additional chemical synthesis steps<br>Insufficient stability in the systemic circulation<br>Relatively low drug loading capacity<br>Premature drug leakage, high potential dissociation of a drug (low retention)<br>Non-homogenous<br>Highly cytotoxic<br>Low stability |
| Dendrimers | A Multi-step synthesis that increases production costs -<br>Complex synthetic route<br>Higher toxicity rate<br>Uncontrolled drug release with encapsulation |
| Metallic Nanoshells | Non-biodegradable-Accumulation in the body,<br>Cause long- term toxicity |

Nanoflowers are flower like structures in nano-size formed by intramolecular interactions between the metal ions and the enzymes/proteins leading to anisotropic growth of nano-petals and, consequently, the formation of a flower-like structure. Nanoflowers are endowed with diverse functionalities for bio-catalytic applications. They represent a new and elegant approach in enzyme immobilization, possessing greatly enhanced activity, stability, durability, and even selectivity of entrapped organic biomolecules. The ultra-rapid, simple synthesis of producing immobilized enzymes acquires the hierarchical nanostructures showing structure similar to a flower with large surface-to-volume ratios (petals bloom). Thus, nanoflowers research is anticipated to take multiple directions for the development of drug delivery systems, biosensors, biocatalysts, and bio-related devices etc.

Inorganic nano-crystals have been widely reported for applications in catalysis and analytical science (Wu et al., 2015). Organic-inorganic hybrid nanoflowers have received much attention due to their simple synthesis, high efficiency, and enzyme stabilizing ability. However, the preparation of enzymatic nanoflowers (organic) from microbial sources are yet to be explored. So far, Horseradish peroxidase, Glucose oxidase, Laccase, Lipase, Lactoglobulin and Trypsin nanoflowers are reported (Ge et al., 2012; Lee et al., 2015). The nanoflowers such as α-lactalbumin, laccase, carbonic anhydrase, and lipase are reported to be used as biosensors (detection tools). They represent the role as bio-catalysis (as enzyme mimetic). Similarly, Wu et al. discloses a facile and rapid method for preparing immobilized Pectate lyases-inorganic hybrid nanoflowers which could improve its bio-catalytic performance.

Fotiadou et al. deals with the routine conventional strategy of using lipase enzyme and immobilizing on the C-based nanomaterials-Graphene oxide (GO), oxidized multi-walled carbon nanotubes (CNTs), and maghemite nanoparticles (γ-Fe2O3) as the support. Thus, the enzyme lipase was not the sole seeding material.

Further, the flowers did not take up proper shape, structure and presented ruptured petals even after final immobilization, and the blooming state of flowers. They can be called microflowers as the size is reported in the range of 15-30 μm.

Thus, no enzymatic nanoflowers which possess a higher degree of cross-linking ability along with displaying a higher propensity in creating nanoflower structure, are reported till date. Further, none of the prior arts till date, suggest a method of preparation of nanoflower utilizing the characteristic properties of Transglutaminase.

OBJECTS OF THE INVENTION

Accordingly, the principal objective of the present invention is to provide novel immobilized Transglutaminase nanoflowers with higher catalytic efficiency without mass transfer limitation.

Still another objective of the present invention is to provide catalytically more active, stable and reusable Transglutaminase nanoflowers.

Yet another objective of the invention is to provide a process for enzymatic designing of Transglutaminase nanoflowers.

Yet another objective of the present invention is to provide a Transglutaminase nanoflower which provides in vivo stability, enhanced bioavailability, higher solubility and absorption in the body, and lowering the adverse effects of drugs.

Another objective of the present invention is to provide a rapid and cost-effective process of preparation of Transglutaminase nanoflower.

Another objective of the invention is to provide floral pockets/cages of TGase nanoflowers as cargo loading sites.

BRIEF DESCRIPTION OF FIGURES AND DRAWINGS

The patent or application file contains at least one drawing executed in color. Copies of this patent or patent application publication with color drawings will be provided by the Office upon request and payment of necessary fee.

The accompanying drawings illustrate some of the embodiments of the present invention and, together with the descriptions, serve to explain the invention. These drawings have been provided by way of illustration and not by way of limitation. The components in the drawings are not necessarily drawn to scale, emphasis instead being placed upon clearly illustrating the principles of the aspects of the embodiments.

SUMMARY OF THE INVENTION

The present invention provides a Transglutaminase nanoflower with higher catalytic efficiency. TGase petals displayed high surface to volume area having 3-D structure. These unique morphological structure, size and desirable features displaying homogenous pockets in TGase nanoflowers were efficiently used to load cargoes (bioactives/drugs) or capture heavy metals.

The present disclosure also provides a simple, non-toxic, biocompatible and cost-effective fabrication process having one-pot green synthesis design and resulting in high enzymatic (TGase) stability, enhanced durability, reusability and bio-catalytic efficiency over a broad range of experimental conditions.

In the present process of designing nanoflowers, Transglutaminase is an organic component that is produced from extremophilic source, *Streptomyces mobaraensis*. Copper (II) is the inorganic metal, wherein incorporated enzyme is not subjected to any denaturant or harsh conditions as compared to other conventional immobilization procedures, thus retaining its bio-catalytic activity.

The present process is designed to replace the current conventional processes which utilize nano-matrices like C-based supports for immobilization along with Bovine Serum Albumin (BSA) proteins and inorganic metallic ions. The present work also highlights the fact that the TGase enzyme is itself acting as a nano-base. In fact, the Transglutaminase serves the dual purpose as a template for nanoflowers and this itself being immobilized. The novel enzymatic bio-nanoconjugates are further provided in the form of blooming nanoflowers.

DETAILED DESCRIPTION OF THE INVENTION

The present invention is now described with reference to the tables/figures and specific embodiments, including the best mode contemplated by the inventors for carrying out the invention. This description is not meant to be construed in a limiting sense, as various alternate embodiments of the invention will become apparent to persons skilled in the art, upon reference to the description of the invention. It is therefore contemplated that such alternative embodiments form part of the present invention.

Unless defined otherwise, technical and scientific terms used herein have the same meaning as commonly understood by one of ordinary skill in the art to which this invention belongs. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Some of the terms are defined briefly here below; the definitions should not be construed in a limiting sense.

The use of "comprise", "comprises", "comprising", "contain", "contains", "containing", "include", "includes", and "including" are not intended to be limiting. It is to be understood that both the foregoing general description and this detailed description are exemplary and explanatory only and are not restrictive.

The term "plurality" as used herein is defined as "one, or more than one". Accordingly, the terms "one", "at least one" would all fall under the definition of "plurality".

Whether or not a certain feature or element was limited to being used only once, either way, it may still be referred to as "one or more features" or "one or more elements" or "at least one feature" or "at least one element".

The term "extremophilic" means an organism that thrives in extreme environments.

The enzymes from extremophilic source are referred to as "extremozymes". They do not get denatured under the extreme harsh conditions and remain active for the cellular bio-catalysis.

The term "actinomycetes" mean a group of gram-positive bacteria such as the *Streptomyces* which form branched filamentous hyphae having resemblance with fungal hyphae.

The term "nanoflowers" defines flower shaped nanocrystals endowed with diverse functionalities for bio-catalytic applications. They signify/depict a special category of nanoscale materials containing a special combination of elements which when viewed microscopically resemble flowers.

The term "iso-peptide" refers to the amide bond that forms between the carboxyl group and an amino group of joining amino acids where at least one of them is part of the side chain.

Accordingly, the present invention provides Transglutaminase nanoflowers and methods of synthesis thereof, which overcome the shortcomings of the prior arts where the Transglutaminase nanoflowers offer the potential to overcome these problems by their multiple synergistic functions of maintaining high specificity and selectivity.

The present novel strategy of designing TGase nanoflowers is an attempt to develop reusable TGase to reduce the cost. Microbial extremophilic Actinomycetes were used as the source to get robust TGase enzyme that is cost-effective as well. The one-pot synthesis design of TGase nanoflowers formation was attempted for the first time for eco-friendly green production, unlike conventional immobilization procedures. The design provides a simple, non-toxic, biocompatible at much less cost fabrication process resulting in high enzymatic (TGase) stability, enhanced durability, reusability and bio-catalytic efficiency.

The present process is designed to replace the current conventional processes which utilize nano-matrices supports and Bovine Serum Albumin (BSA) proteins and inorganic metallic ions as a base for immobilization of enzymes. The present work achieves minimization of the components in designing and rendering the simplest design strategy. The novelty highlights the fact that a major role is played by only the TGase enzyme in sufficing nano-base/platform to take up the nanoflower form. In fact, the TGase serves the dual purpose as a template for nanoflowers and the enzyme itself being immobilized. The novel enzymatic bio-nanoconjugates (TGase nanoflowers) are optimized to adopt the blooming nanoflowers.

The present invention provides the designing of a bio-catalytically active enzymatic TGase nanoflowers from the microbial source at a low temperature of 4° C. TGase serves as a glue that binds the petals together in the nanoflowers. The enzyme TGase is structured in the shape of a flower— the blooming nanoflowers. The TGase mediated nanoflowers display high cargo capacity in the uniform cages/pockets in between petals of pretty nanoflowers.

In one embodiment the invention provides immobilized TGase nanoflowers comprising Transglutaminase and an inorganic metal, wherein the overall flower is in the nano-range, is homo-dispersed and small-sized, and wherein Transglutaminase functions both as a cross-linking enzyme and as a seeding template, and wherein said nanoflowers can tolerate cold temperature and possess higher durability in terms of organic solvents, temperature, pH, storage and operational stability having higher catalytic efficiency of 6.92 fold as compared to free Transglutaminase without any mass transfer limitation.

In another embodiment, the size of the nanoflowers is <50 nm.

In yet another embodiment, the catalytic efficiency of the nanoflowers is 6.92 fold higher as compared to free TGase.

In another embodiment, the source of Transglutaminase is extremophilic actinomycetes *Streptomyces mobaraensis*.

In yet another embodiment said inorganic metal is selected from the group comprising zinc, iron, manganese, magnesium, potassium, calcium and copper.

In a preferred embodiment said inorganic metal is copper.

In another embodiment said nanoflower is homo-dispersed and less than 50 nm in size.

In another embodiment said nanoflowers have uniform cages/pockets in between the petals.

In another embodiment said nanoflower is bio-catalytically active.

In another embodiment the nanoflowers display a 3-D structure.

In another embodiment the activity of the nanoflower is 156.74% folds to that of free enzyme TGase.

In yet another embodiment the structure of the petals is porous in nature.

In another embodiment, the nanoflower retains the activity even after the tenth cycle.

In another embodiment said nanoflowers display controlled and targeted release of bioactive drugs and heavy metals.

Yet another embodiment of the present invention is a one-pot green synthesis process for designing the Transglutaminase nanoflower comprising the steps of:
 a. solubilizing 200 µl $CuSO_4$ in Milli-Q water;
 b. adding to 30 ml of 2×PBS (pH-7.4) with 3 mg/ml enzyme Transglutaminase;
 c. incubating the solution from step b for three days at 4° C.;
 d. sonicating the suspension obtained from step c for 15 min;
 e. drying and filtering to obtain the immobilized extremozyme Transglutaminase nanoflowers.

In another embodiment, the Transglutaminase enzyme in the process as defined above is itself the seeding template of the nanoflowers which is also responsible for cross-linking apart from being immobilized in the form of nanoflowers.

The present invention utilizes a combination of the functionality of immobilization material with the biological activity of Transglutaminase together with its characteristics of site-specific delivery along with the sustained and controlled release. Immobilizing extremozyme Transglutaminase in form of nanoflowers leads to higher catalytic efficiency without mass transfer limitation. It is important to note that TGase is the base (organic) here rather than the inorganic metal centre.

Interestingly, the complex occurs between copper ions and TGase leads to the nucleation in presence of PBS for primary crystals formation. The mechanism for nanoflower is envisioned to be the coordination bonding of copper ions (Cu') with amide groups present in the TGase backbone. On their interaction, transformation takes place leading to growth and assembly in the form of flower shaped petals. TGase gets confined in the nanoflowers, exhibiting enhanced enzymatic activity and remarkably higher stability compared with free TGase enzyme.

The inventors also emphasize that these branched flower shaped nanoflower having anisotropic growth process with TGase, mimics the nature's blooming state from small buds. Hence, TGase being a cross-linking enzyme is responsible to induce the nucleation of copper phosphate crystals and forming a glued scaffold for petals. For instance, FIG. 2 portrays the mechanism of growth of Transglutaminase nanoflowers. Further, TGase with inherent cross-linking ability have a higher propensity to them in spontaneously creating nanoflower structure much more easily as compared to other enzymes or proteins where the TGase serves as a glue that binds the petals together in the nanoflower.

Interestingly, structural stability in different organic solvents (methanol, ethanol, propanol, DMSO), thus hydrophilic molecules can also be delivered. Hence, the enzyme-inorganic hybrid TGase nanoflowers, with combined functionalities of protein and inorganic component will have an important role in the biomedical field for drug delivery and other applications.

TGase nanoflowers are expected to combat the prevailing delivery systems major challenges, including in vivo instability, poor bioavailability, and poor solubility, poor absorption in the body, issues with target-specific delivery, and tonic effectiveness, and probable adverse effects of drugs.

Hence, blooming of the TGase nanoflowers will be a very promising nano-vehicle in the near future.

There are a number of advantages of the TGase nanoflowers as compared to native TGase. Microbial TGases are monomeric proteins made up of 331 amino acids with a molecular weight of 38 kDa. These are a member of α+β folding class, with 10 α-helices and 8 β-strands. They have a disk-like structure with a central groove having the active-centre with a Cys-His-Asp triad. The wide active-site cleft accommodates the alpha-helix, leading to the broader substrate specificity with a higher reaction rate, which is the key to its cross-linking efficiency. The TGase enzyme structure presents a backbone more likelihood to acquire characteristic flower like shape. The configuration of TGase enzyme will lead to shape nanoflowers shape.

By virtue of having a wider range of properties and considering all the above-mentioned factors, nanoflowers have the following added advantages:
 Inherent cross-linking capability which can transform them into a good delivery vehicle
 Tagged with GRAS (generally recognized as safe) status
 Desirable size, petals display high surface to volume area and 3-D structure as delivery for high load cargo
 These qualities are not possible with or possessed by the native TGase.

The present disclosure with reference to the following accompanying examples describes the present invention. However, those of skill in the art should, in light of the present disclosure, appreciate that many changes can be made in the specific embodiments which are disclosed and still obtain a like or similar result without departing from the spirit and scope of the invention. It is understood that the examples are provided for the purpose of illustrating the invention only, and, are not intended to limit the scope of the invention in any way.

EXAMPLES

Materials:

Streptomyces mobaraensis NCIM 5208 was procured from National Collection of Industrial Microorganisms (NCIM), National Chemical Laboratory, Pune, India. The culture was maintained on MGYP (containing g/L: malt extract 3, glucose 10, yeast extract 3 and peptone 5, adjusted to pH-6.0) slants and stored at 4° C. The strain was routinely sub-cultured for the production of enzyme Transglutaminase. In all experiments, enzyme Transglutaminase was indigenously produced from this culture after optimizing the production of the enzyme. All analytical grade chemicals were purchased from Sigma Aldrich (St Louis, USA). All stock solutions were prepared with MilliQ-purified distilled water.

Example 1: Preparation of TGase Nanoflowers

To carry out the synthesis of TGase nanoflowers, 200 μl of aqueous $CuSO_4$ solution (240 mM) in Milli-Q water was added to 30 ml of PBS (2×, pH-7.4) containing 3 mg/ml TGase enzyme, followed by incubation at 4° C. for three days. The processing of nanoflowers was carried by sonicating the suspension for 15 min, later dried and filtered for characterization and applications.

The design of bud to blooming nanoflowers was finalized after optimizing various parameters. The possible range for the parameters in the study was analyzed and tested, varying the concentration, volume, temperature, pH, and incubation time etc. The changes were noticed in the morphology and characteristics of nanoflowers on account of interplaying factors, for example, the seeding component, TGase, varied from 0.1-12 mg/ml; $CuSO_4$ from 0.1 mM, 1 mM, 25 mM, 50 mM, 120 mM, 240 mM, 0.500 mM; temperature range was 4, 8, 15, 25, 30, 35, 50° C.; pH spectrum from acidic to alkaline (3, 5, 7, 8, 9) etc. were taken in consideration to check the robustness of nanoflowers. The enzyme produced from the microbial source Streptomyces mobaraensis NCIM 5208 was utilized for the experimentation.

The process was accelerated so that the design template can be observed in the form of crystals which after three days, formed perfect nanoflowers. TGase nanoflowers were able to tolerate cold temperature and had higher durability.

It should be noted that Transglutaminase serves the dual purpose firstly, as a template (support) of nanoflowers and secondly, the enzyme itself get immobilized in nanoflowers during the process.

Figure 2:
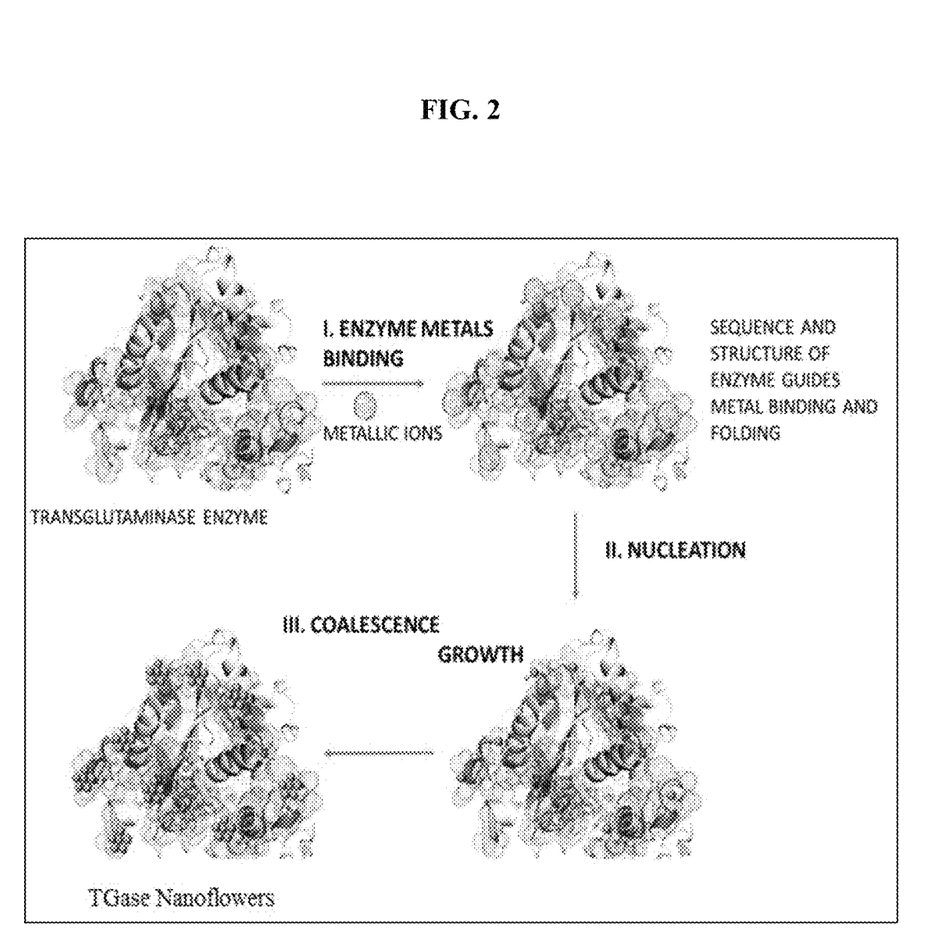
FIG. 2 illustrates the mechanism of Transglutaminase nanoflowers (TGase-NFs) synthesis.

The synthesis was carried out at a very low temperature (4° C.). The present disclosure for the first time reports the synthesis of nanoflowers at such a low temperature (FIG. 2).

Results:

The TGase nanoflowers appeared within a few hours in the bud stage, it bloomed completely on the third day and envisaged to present a higher loading capacity of cargo for delivery of bioactives or drugs along with being non-toxic and biocompatible. With its controlled release of cargo, targeted binding and delivery can be achieved; hence lowering the chances of any undesirable immunogenic reactions.

Further, the high surface area to volume ratio presented by nanoflowers not only enhances the surface adsorption for accelerating the kinetics of bio-catalytic reactions, but also adds to higher loading and better charge transfer owing to its 3-D structure.

Bovine serum albumin (BSA) is used as the standard protein component ever since the metallic nanoflowers came into being. The uniqueness/novelty of the present strategy was the replacement of the BSA protein base by TGase itself, thereby leading to unique morphology and size of the nanoflowers, after optimizing the concentration of TGase, ageing time, sonication, pH, temperature, PBS and $CuSO_4$ concentration (Table 2). The table below depicts the comparative properties of enzymatic TGase nanoflowers with Lipase nanoflowers from the prior art.

TABLE 2

Comparative properties of TGase nanoflowers with Lipase nanoflowers

| CHARACTERISTIC PROPERTIES | LIPASE NANOFLOWERS | TGase NANOFLOWERS |
|---|---|---|
| Seeding Template (nano-support) | C-based nanomaterials-Graphene oxide (GO), oxidized multi-walled carbon nanotubes (CNTs), and maghemite nanoparticles ($\gamma$-$Fe_2O_3$) as nano-support rather than just lipase enzyme | Enzyme Transglutaminase solely ordains the morphology on the basis of its molecular weight and TGase enzyme stereochemistry and structure |
| Size and Shape Morphology | Large: Micro-range (15-30 μm) (Pseudo microflowers): Ruptured flakes of petals; no cage | Small: Nano-range (<50 nm) open petals (cages) True nanoflowers: Blooming, |
| Temperature for synthesis | High (25° C.) | Low (4° C.) |
| Stability | Very low (19.2% activity at 60° C.) | Very High (62.9% activity retained at 80° C., storage stability at 25° C.: 87.3% activity maintained even after 60 days) |
| Activity | 83% residual activity (15.04% higher) | 156.74% higher catalytic activity) |
| Metal Ion effect | Present (high influence) | Absent |
| Reusability/recovery | Low (8th cycle) | Yes (10$^{th}$ cycle), >95% recovered |

TABLE 2-continued

Comparative properties of TGase nanoflowers with Lipase nanoflowers

| CHARACTERISTIC PROPERTIES | LIPASE NANOFLOWERS | TGase NANOFLOWERS |
|---|---|---|
| Durability | No (80.8% activity loss in just 5 h incubation at 60° C.) | Yes (very high, sustained harsh conditions like acidic and alkaline pH, temperature >60° C. for 1 h, organic solvents: methanol, ethanol, propanol, DMSO); robust |
| Cargo loading property | Absent | Very High with site-specific, controlled release, the nanoflowers pockets were uniformly loaded with the cargo (yield was >98%) |

Example 2: Optimization of Transglutaminase Nanoflower Design

Figure 3:
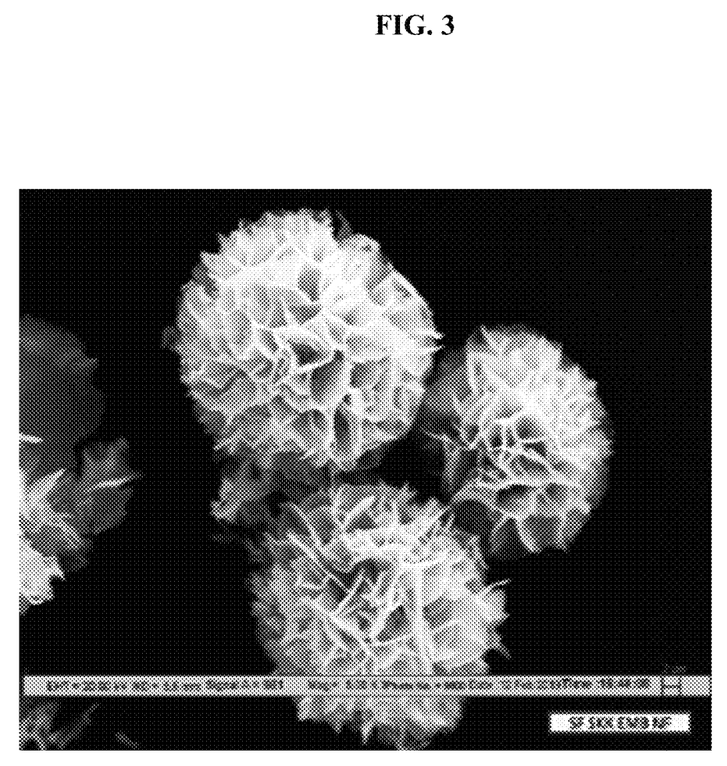
FIG. 3 shows the formation of TGase-incorporated $CuSO_4$ nanoflowers captured by Scanning Electron Microscope (SEM) images under optimized reaction conditions (240 mmol $L^{-1}$ $Cu^{2+}$, 0.1 mol $L^{-1}$ PBS at pH 7.4, 0.3 mg TGase at 4° C.).
Figure 4:
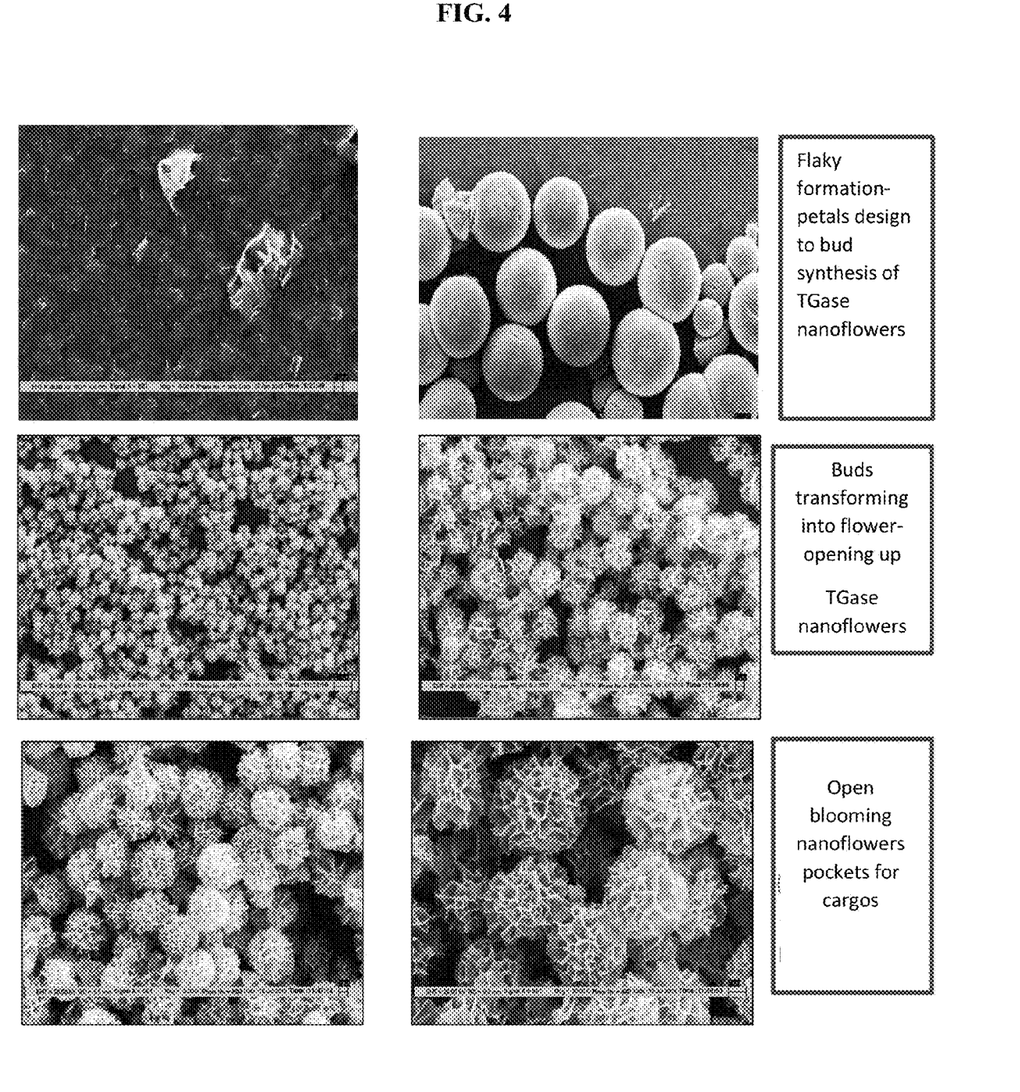
FIG. 4 illustrates the architecture of TGase nanoflowers. Scanning Electron Microscope (SEM) images under optimized reaction condition capturing the stages in the formation of TGase mediated nanoflowers-bud to blooming stages of nanoflowers.

The design of TGase nanoflowers under optimized reaction conditions is highlighted in FIG. 3, which shows the formation of TGase-incorporated $CuSO_4$ nanoflowers captured by Scanning Electron Microscope (SEM) images under optimized reaction conditions (240 mmol U' $Cu^{2+}$, 0.1 mol U' PBS at pH 7.4, 0.3 mg TGase at 4° C.). High-resolution of the porous structure of the petals was observed. The stages during the formation of TGase mediated nanoflowers were well captured from flaky initiation to bud and later transforming into full-bloomed nanoflowers (FIG. 4). The essence of enzyme TGase in nanoflowers was that its structure dictated the unique 3-D floral pattern. TGase served as a molecular glue to bind the petals together in the nanoflowers. Copper ions where inorganic element for initialization of nanoflowers, acted as chelating ions.

Example 3: Characterization of Transglutaminase Nanoflower

Figure 5:
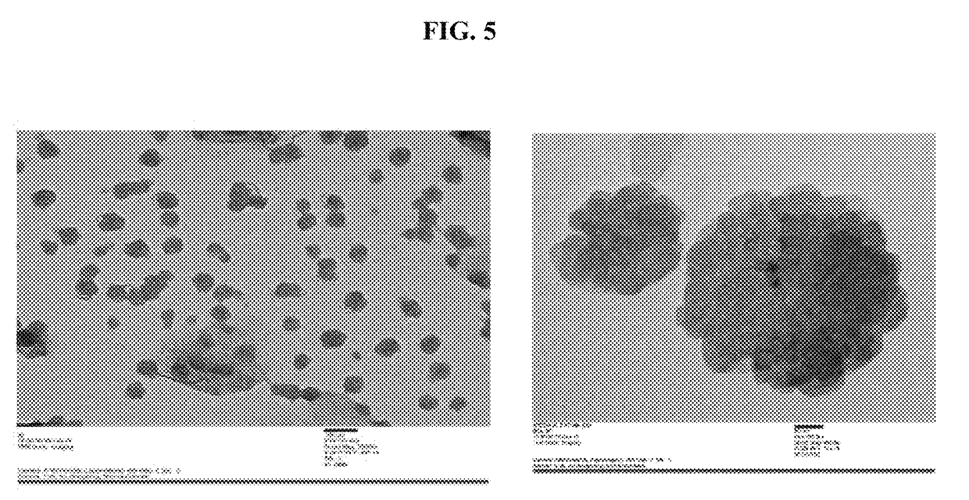
FIG. 5 shows the analysis of TGase nanoflowers depicting uniform size using Transmission Electron Microscopy (TEM).
Figure 6:
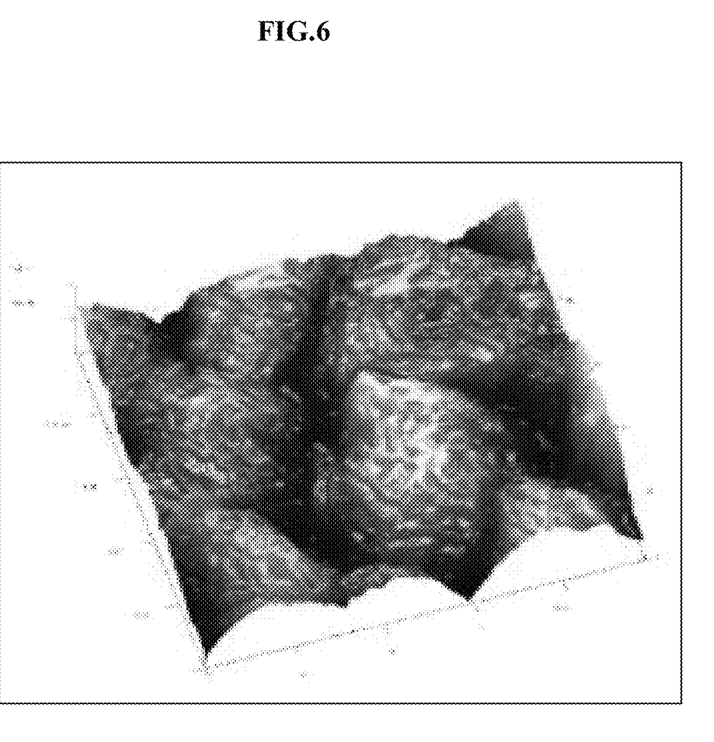
FIG. 6 shows the surface analysis in terms of topology and roughness measured by Atomic force microscope (AFM).

Characterization for size, shape/morphology, surface, microstructure, stability and other physico-chemical attributes was carried out by SEM, TEM, DLS, XRD, FT-IR, TGA, AFM etc. The characterization for the size of TGase nanoflowers was carried out by Transmission Electron Microscopy (TEM) analysis (FIG. 5). The image clearly showed the uniform size distribution of TGase nanoflowers. The nucleation process was also remarkably marked by TEM micrographs. The TEM validated the nanoflowers being homo-dispersed and small-sized (<50 nm). The surface analysis in terms of topology and roughness was measured by Atomic Force Microscope (AFM) (FIG. 6). The surface of TGase nanoflowers petals completely blooming was framed in AFM.

Results:

The study discloses the synthesis of a new nanoflower hybrid from Transglutaminase and copper sulphate at lowest temperature (4° C.), which in turn provides catalytically more active, stable and reusable Transglutaminase nanoflower. It has an interesting flower-like structure on the nano-scale. Its properties were examined, and the results showed that they exhibited a higher catalytic activity vis-a-vis enhanced operational stability in the resolution reaction as compared with the free TGase enzyme.

The TGase nanoflowers have high surface area and 3-D structure for possible confinement of bioactives and drug load which is not exhibited in Transglutaminase native form.

Moreover, Transglutaminase when used in nanoflower form, exhibited an increment in its activity, 156.74% folds of that of free enzymes (3.14 IU/ml) along with displaying effective durability and reusability, highlighting its potential for repeated uses. It was found that their activity was retained even after the tenth cycle of reuse. Significant improvement in kinetic parameters (catalytic efficiency was found to be 6.92 fold higher than free TGase) and stability was also observed where it could tolerate extreme pH/temperature/solvents/ultrasonic pressure) as stable nanoflowers (Table 3).

TABLE 3

Kinetic Parameters of Free Transglutaminase enzyme and Immobilized nanoflowers form

| Kinetic Parameter of Transglutaminase enzyme | Free form (Control) | Nanoflowers form (immobilized) | Fold Change |
|---|---|---|---|
| Vmax (mM $min^{-1}$) | 10.69 | 19.03 | ↑ 1.78 |
| Km (mM) | 14.78 | 3.80 | ↓ 0.26 |
| Catalytic Efficiency (Vmax/Km) | 0.72 | 5.01 | ↑ 6.92 |

The TGase was assayed as described in Fatima & Khare 2019.

Standard TGase nanoflowers displayed designs which had close pockets so as to carry the cargo/attach bioactive/drug. Other reported nanoflowers had an issue of size and closed caged morphology, which limited their use as a nano-carrier (Table 2).

The nanoflower obtained were intact, robust, and highly resistant due to iso-peptide bond of TGase that sustained the degradation process. Thus, floral shape remained preserved even at harsh conditions which is not true for any other nanoflowers being claimed earlier.

Example 4: Comparison with Other Enzyme Nanoflowers with Various Metals

In the present invention, Transglutaminase enzyme was primarily used as the seeding template. However, the previous studies depict the preparation of enzyme nanoflower with the routine conventional strategy of using proteins/enzymes and immobilizing on the nano-matrix such as C-based nanomaterials-Graphene oxide (GO), oxidized multi-walled carbon nanotubes (CNTs), and maghemite nanoparticles (γ-Fe2O3) as the support, which proves that enzymes were not the sole seeding material, and were designed and formulated on nano-support with the help of inorganic metals.

Further, the site-specific cross-linking activity based on Gln-Lys of Transglutaminase- has not been exploited in synthesizing nanoflowers. The TGase portrayed higher propensity in spontaneously creating nanoflowers by its cross-linking activity over other enzymes.

Figure 7:
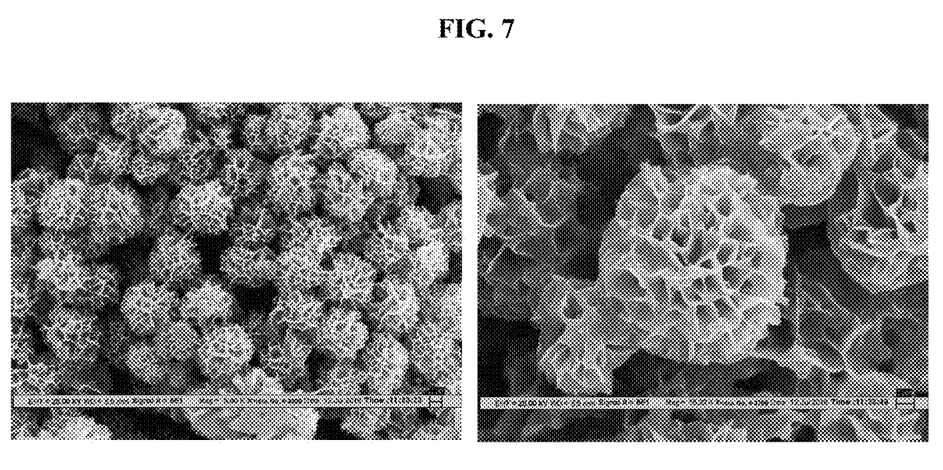
FIG. 7 shows the SEM images showing TGase nanoflowers having iron and zinc ions respectively with TGase as a seeding template.

It was also observed that copper ion acts only as a chelating agent which are required for initialization of nanoflowers synthesis. After replacing copper with other inorganic metal ions like zinc, iron, manganese, magnesium, potassium, calcium the study effectively demonstrated that only the enzyme was the influencing factor for nanoflower rather than copper as the same size and morphology were noticed using TGase with zinc or iron or manganese. Thus, the present study proved that the main influence was of organic part-enzyme and not of inorganic metals (FIG. 7).

It was also observed that extremozyme TGase was solely responsible for nanoflowers structure, the enzyme itself is getting folded to the floral appearance on account of its structure. Intact, robust, highly resistant nanoflower were resulted due to iso-peptide bond of TGase which could sustain the degradation process. Thus, flower shape remained preserved even at harsh conditions which is not true for any previously reported nanoflowers. The previous studies depicted that their flowers have not taken up the proper shape, structure and represented ruptured petals even after final immobilization, one cannot observe the blooming state of flowers.

Further, the previous studies on nanoflowers, more precisely termed as microflowers carried out processing of pseudo nanoflowers at high temperature (35° C.) by lyophilization or drying over vacuum to preserve the integrity of delicate bioconjugates. However, the source of TGase nanoflowers in the present invention was from extremophilic actinomycetes *Streptomyces*, hence nanoflowers were synthesized at low temperature (4° C.) wherein the drying did not even partially disrupt the shape and structure.

It was observed that even after functionalization, the nanoflowers remained robust and fully intact in their original form. This also gives an advantage to a broader range of applicability under harsh conditions.

Example 5: Validation of Transglutaminase Nanoflower

Figure 8:
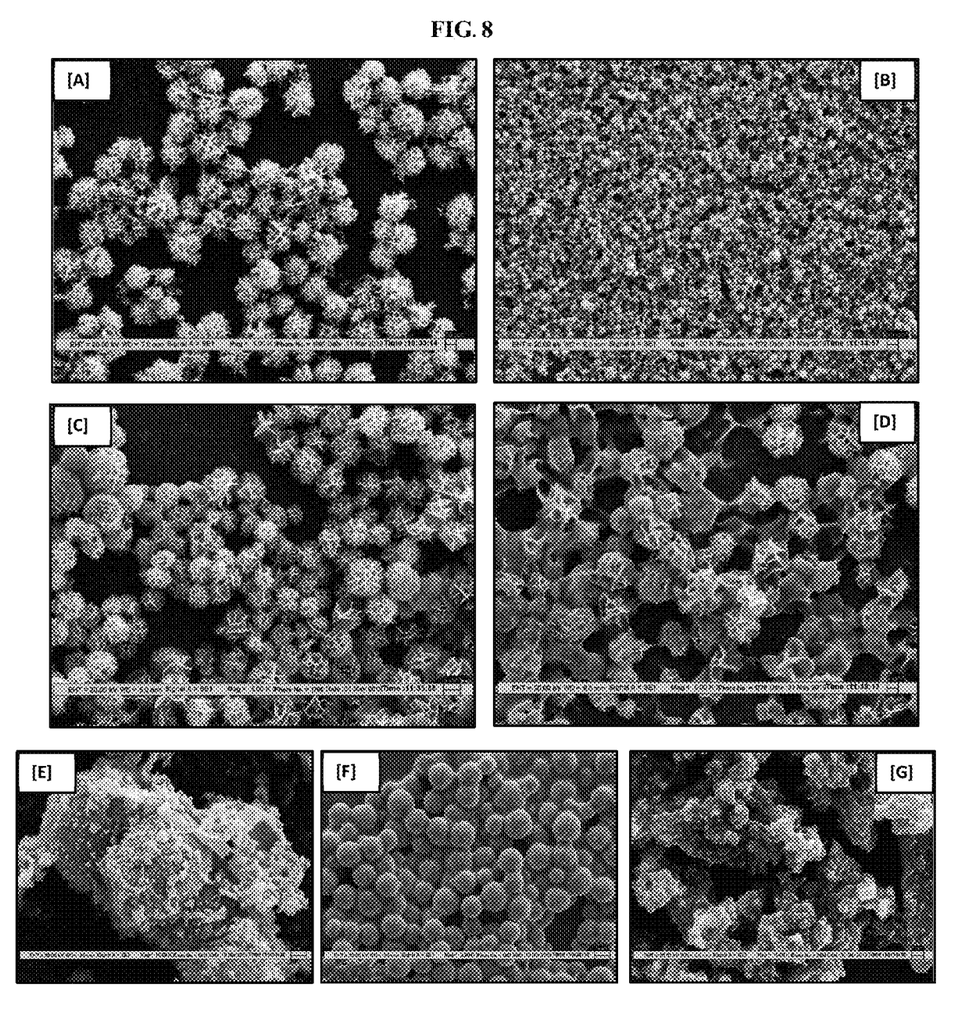
FIG. 8 shows efficient cargo loading on TGase nanoflowers captured by Scanning Electron Microscope (SEM) images (A: control without cargo; B-D: drug-Doxorubicin; E-F: heavy metals absorbed from waste-water).

TGase nanoflowers floral pattern was successfully utilized in various applications of loading different cargoes where it was shown to be efficient in high cargo loading as depicted by FIG. 8. The utility of these petal pockets/cages was characterized by SEM analysis. The FIG. 8 [A] is control-TGase nanoflowers without any cargo loaded, whereas FIG. 8 [B-D] shows the loading of anti-cancer drug-Doxorubicin; FIG. 8 [E-F] heavy metals remediated from waste-water effluents.

Figure 9:
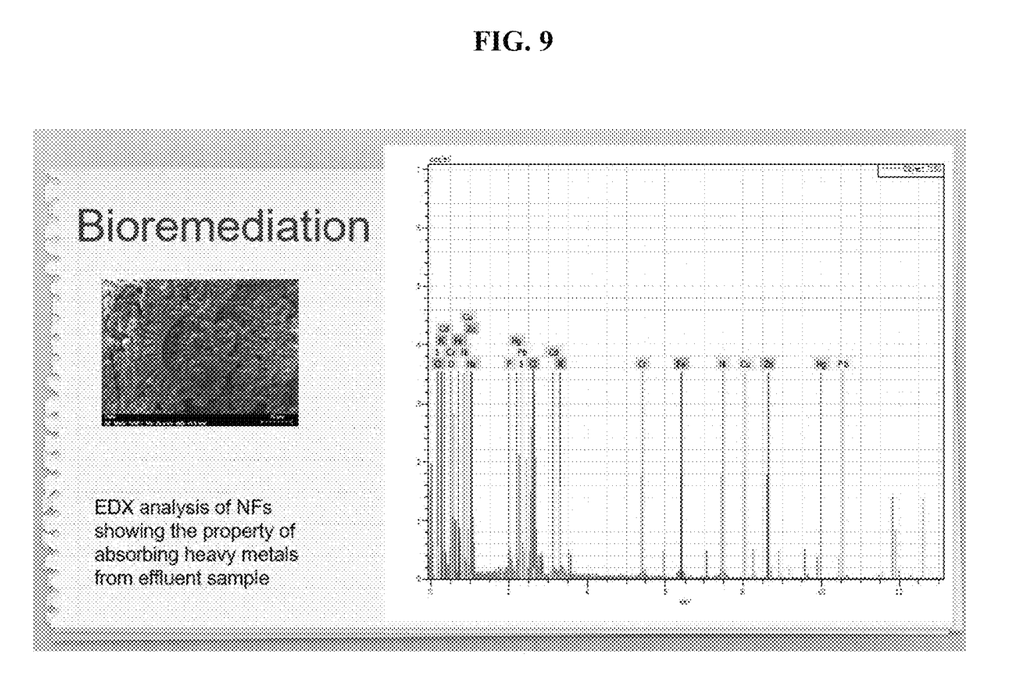
FIG. 9 displays the application of TGase nanoflowers in remediation with simulated as well as real waste-water effluents.

Further, the application of nanoflowers in therapeutics and heavy metals remediation was done which showed an effective loading of cargos (metals/drugs/DNA) were loaded in uniform nanoflowers pockets endorsing the site-specific delivery/remediation agent, possible by TGase nanoflowers only. For instance, FIG. 9 depicts the application of TGase nanoflowers in remediation. The verification was done by EDX and SEM analysis after treatment was carried out with simulated as well as real waste-water effluents. The effluents got captured in their floral pockets. Heavy metals were quenched in TGase nanoflowers.

Figure 10:
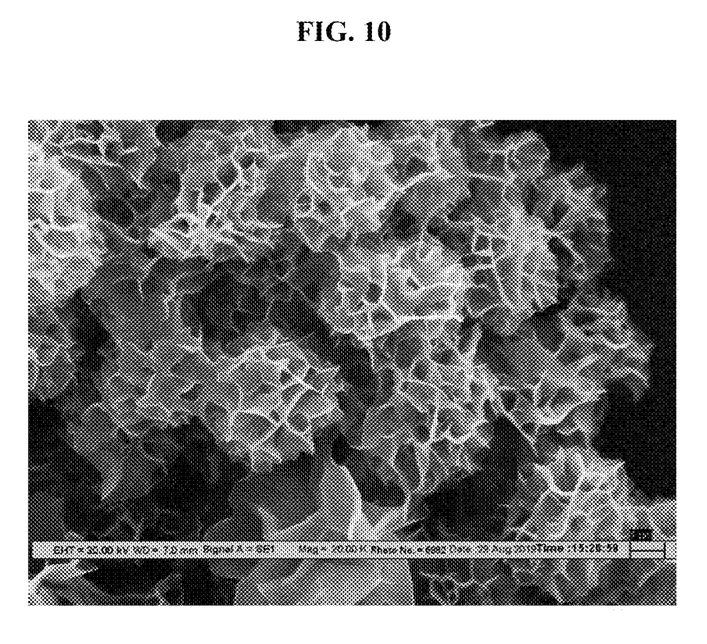
FIG. 10 shows the intact TGase nanoflowers after functionalization or after harsh environment.

In terms of the morphology of the Transglutaminase nanoflower, TGase nanoflowers were found to be robust and durable to resist even harsh environmental conditions-high temperature, solvent, pH fluctuations etc. as shown in FIG. 10. Even after functionalization or application in capturing heavy metals from waste-water, the morphology remained intact. They were also found to be solvent stable. They retained their structural integrity in different organic solvents tested like methanol, ethanol, propanol, DMSO. Even after undergoing the processing during their applications, it did not impact the characteristics of nanoflowers.

Results:

There are a number of advantages of the TGase nanoflowers as compared to native TGase. Microbial TGases are monomeric proteins composed of 331 amino acids. It has a molecular weight of 38 kDa. These are member of $\alpha+\beta$ folding class, with 10 $\alpha$-helices and 8 $\beta$-strands. The characteristic features of TGase with the secondary structure of a classical $(\alpha/\beta)8$ sheets have a disk-like structure with a central groove. The active-centre is comprised with a Cys-His-Asp triad. The wide active-site cleft accommodates the alpha-helix, leading to the broader substrate specificity with a higher reaction rate, which is the key to its cross-linking efficiency.

This structural information reveals the presence of conserved amino acid residues responsible for TGase catalytic activity. Microbial TGase active site is specifically characterized by unique predominance of acidic (4 Asp and 2 Glu), aromatic and hydrophobic residues (7 Trp).

The study represented that TGase nanoflowers had higher encapsulating yield, higher protein ratio and enzyme efficiency than any other enzyme based nanoflowers till date. Moreover, Transglutaminase in nanoflower form, exhibited an increment in its activity, 156.74% folds of that of free enzymes (3.14 IU/ml) along with displaying effective durability and reusability, highlighting its potential for repeated uses. Hence, these TGase nanoflowers was found to be a promising nano-vehicle for controlled and targeted delivery.

In the present invention, the overall flower has been optimized in the nano-range that too being homo-dispersed and small-sized i.e. <50 nm as validated by TEM. This marks the novelty of our invention, which can be useful for translational medicinal applications. Unlike the earlier studies, the flakes representing petals of nanoflowers are also in nano-range which is observed in SEM micrographs and the overall flowers designed resulted after optimizing the parameters even with the application of binding and loading cargo lies in nano-range. Hence, the present invention demonstrated for the first time the fully bloomed nanoflowers which even after being implemented in various application as a function of carrier holds valid in true sense depicting/retaining the true nanoflower characteristics.

ADVANTAGES

The present invention offers the following advantages:
Drugs-bioactives/anti-cancer agents for targeted delivery.
Capture heavy metals/pollutants for bioremediation application (waste-water treatment).
TGase mediated nanoflowers worked really well in targeted activity based on the good drug efficacy being loaded onto it.
They showed controlled and sustained release of cargo (drugs and heavy metals).
TGase being a versatile unconventional enzyme gave a distinct functionality to nano-modality created in form of nanoflowers.

REFERENCES

Ajorlou, E. and Khosroushahi, A. Y., 2017. Trends on polymer- and lipid-based nanostructures for parenteral drug delivery to tumors. Cancer chemotherapy and pharmacology, 79(2), pp. 251-265.

Chan, S. K. and Lim, T. S., 2019. Bioengineering of microbial transglutaminase for biomedical applications. Applied microbiology and biotechnology, 103(7), pp. 2973-2984.

Duarte, L., Matte, C. R., Bizarro, C. V. and Ayub, M. A. Z., 2020. Review transglutaminases: part II—industrial applications in food, biotechnology, textiles and leather products. World Journal of Microbiology and Biotechnology, 36(1), pp. 1-20.

Fatima, S. W. and Khare, S. K., 2018. Current insight and futuristic vistas of microbial transglutaminase in nutraceutical industry. Microbiological research, 215, pp. 7-14.

Fatima, S. W., Tiwari, R. and Khare, S. K., 2019. Utilization of agro-industrial waste for production of Transglutaminase from *Streptomyces mobaraensis*. Bioresource technology, 287, p. 121391.

Folk, J. E. and Cole, P. W., 1965. Structural requirements of specific substrates for guinea pig liver transglutaminase. Journal of Biological Chemistry, 240(7), pp. 2951-2960.

Gajšek, M., Jančič, U., Vasić, K., Knez, . and Leitgeb, M., 2019. Enhanced activity of immobilized transglutaminase for cleaner production technologies. Journal of Cleaner Production, 240, p. 118218.

Ge J., Lei. J., and Zare R. 2012. Protein-inorganic hybrid nanoflowers. Nature Nanotechnology, 7, pp. 428-432.

Irimie, A. I., Sonea, L., Jurj, A., Mehterov, N., Zimta, A. A., Budisan, L., Braicu, C. and Berindan-Neagoe, I., 2017. Future trends and emerging issues for nanodelivery systems in oral and oropharyngeal cancer. International journal of nanomedicine, 12, p. 4593.

Lamberti, M., Zappavigna, S., Sannolo, N., Porto, S. and Caraglia, M., 2014. Advantages and risks of nanotechnologies in cancer patients and occupationally exposed workers. Expert opinion on drug delivery, 11(7), pp. 1087-1101.

Lee, S. W., Cheon, S. A., Kim, M. I. and Park, T. J., 2015. Organic-inorganic hybrid nanoflowers: types, characteristics, and future prospects. Journal of nanobiotechnology, 13(1), pp. 1-10.

Miwa, N., 2020. Innovation in the food industry using microbial transglutaminase: Keys to success and future prospects. Analytical Biochemistry, p. 113638.

Rana, V. and Sharma, R., 2019. Recent advances in development of nano drug delivery. In Applications of Targeted Nano Drugs and Delivery Systems (pp. 93-131). Elsevier.

Wu, X., Hou, M. and Ge, J., 2015. Metal-organic frameworks and inorganic nanoflowers: a type of emerging inorganic crystal nanocarrier for enzyme immobilization. Catalysis Science & Technology, 5(12), pp. 5077-5085.

Wu, P., Luo, F., Lu, Z., Zhan, Z. and Zhang, G., 2020. Improving the Catalytic Performance of Pectate Lyase Through Pectate Lyase/Cu3 (PO4) 2 Hybrid Nanoflowers as an Immobilized Enzyme. Frontiers in Bioengineering and Biotechnology, 8, p. 280.

We claim:

1. Immobilized Transglutaminase nanoflowers, comprising:
   Transglutaminase and an inorganic metal, wherein the overall flower is in the nano-range, is homo-dispersed and small-sized, and wherein
   the transglutaminase is a template for the formation of the flowers that are immobilize to the structure of the transglutaminase, and
   wherein said nanoflowers can tolerate cold temperature and possess higher durability in terms of organic solvents, temperature, pH, storage and operational stability, having higher catalytic efficiency of 6.92 fold as compared to free Transglutaminase without any mass transfer limitation.

2. The nanoflower as claimed in claim 1 wherein the size of the nanoflowers is <50 nm.

3. The nanoflower as claimed in claim 1 wherein the source of Transglutaminase is extremophilic actinomycetes *Streptomyces mobaraensis*.

4. The nanoflower as claimed in claim 1, wherein said inorganic metal is selected from the group comprising zinc, iron, manganese, magnesium, potassium, calcium and copper.

5. The nanoflower as claimed in claim 1, wherein said inorganic metal is copper.

6. The nanoflowers as claimed in claim 1, wherein said nanoflower is homo-dispersed and less than 50 nm in size.

7. The nanoflowers as claimed in claim 1, wherein said nanoflowers have uniform cages/pockets in between the petals.

8. The nanoflowers as claimed in claim 1, wherein said nanoflower is bio-catalytically active.

9. The nanoflowers as claimed in claim 1, wherein nanoflowers display a 3-D structure.

10. The nanoflowers as claimed in claim 1, wherein the activity of the nanoflower is increased 156.74% over free TGase.

11. The nanoflower as claimed in claim 1, wherein the structure of the petals is porous in nature.

12. The nanoflowers as claimed in claim 1, wherein the nanoflower retains the activity even after ten cycles.

13. The nanoflowers as claimed in claim 1, wherein said nanoflowers display controlled and targeted release of bioactive drugs and heavy metals.

14. A one-pot green synthesis process for designing the Transglutaminase nanoflower of claim 1, said process comprising the steps of:
   a. solubilizing 200 ul $CuSO_4$ in Milli-Q water;
   b. adding to 30 ml of 2×PBS (pH-7.4) with 3 mg/ml enzyme Transglutaminase;
   c. incubating the solution from step b for three days at 4° C.;
   d. sonicating the suspension obtained from step c for 15 min;
   e. drying and filtering to obtain the immobilized Transglutaminase nanoflowers.

15. The process as claimed in claim 14, wherein the transglutaminase is a template for the formation of the flowers that are immobilize to the structure of the transglutaminase.

* * * * *